(12) United States Patent
Bhullar et al.

(10) Patent No.: US 7,473,398 B2
(45) Date of Patent: Jan. 6, 2009

(54) BIOSENSOR

(75) Inventors: Raghbir S. Bhullar, Indianapolis, IN (US); Christopher D. Wilsey, Carmel, IN (US); John T. Austera, Indianapolis, IN (US); Wolfgang O. L. Reiser, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 915 days.

(21) Appl. No.: 09/866,030

(22) Filed: May 25, 2001

(65) Prior Publication Data

US 2002/0192115 A1    Dec. 19, 2002

(51) Int. Cl.
    *G01N 30/00*    (2006.01)
(52) U.S. Cl. .................... 422/82.01; 422/50; 422/99
(58) Field of Classification Search ............. 422/82.01, 422/56, 58, 61, 68.1, 82.02, 50, 99; 435/817; 204/403.01, 409; 205/777.5
See application file for complete search history.

(56) References Cited

U.S. PATENT DOCUMENTS

| | | | |
|---|---|---|---|
| 3,868,534 A * | 2/1975 | Pighin et al. ................. 313/483 |
| 4,233,029 A | 11/1980 | Columbus .................... 23/230 |
| 4,849,340 A | 7/1989 | Oberhardt .................... 435/13 |
| 4,963,814 A | 10/1990 | Parks et al. .................. 323/274 |
| 4,999,582 A | 3/1991 | Parks et al. .................. 324/438 |
| 4,999,632 A | 3/1991 | Parks .......................... 341/167 |
| 5,120,420 A * | 6/1992 | Nankai et al. ........... 204/403.11 |
| 5,243,516 A | 9/1993 | White .................... 364/413.07 |
| 5,352,351 A | 10/1994 | White et al. ................. 204/406 |
| 5,366,609 A | 11/1994 | White et al. ................. 204/403 |
| 5,405,511 A | 4/1995 | White et al. ............. 204/153.1 |
| 5,413,690 A | 5/1995 | Kost et al. .................... 204/403 |
| 5,438,271 A | 8/1995 | White et al. ................. 324/444 |
| 5,512,159 A | 4/1996 | Yoshioka et al. ............ 204/403 |
| 5,628,890 A | 5/1997 | Carter et al. ................. 204/403 |
| 5,762,770 A | 6/1998 | Pritchard et al. ............ 204/403 |
| 5,798,031 A | 8/1998 | Charlton et al. ............. 204/403 |
| 5,965,001 A | 10/1999 | Chow et al. .................. 204/600 |
| 5,997,817 A | 12/1999 | Crismore et al. .............. 422/58 |

(Continued)

FOREIGN PATENT DOCUMENTS

EP    0 359 831 A    3/1990

(Continued)

OTHER PUBLICATIONS

LPKF MicrolineLaser II, LPKF Laser & Electronics AG; LPKF; Art.-Nr. 107645-2 (Jan. 2000) (2pp.).

(Continued)

*Primary Examiner*—Sam P Siefke
(74) *Attorney, Agent, or Firm*—Justin L. Sage; Roche Diagnostics Operations, Inc.

(57) ABSTRACT

The present invention relates to a biosensor. The biosensor includes a support substrate having first and second ends, electrodes positioned on the support substrate, the electrodes cooperating with one another to define electrode arrays situated adjacent to the first end, a spacer substrate positioned on the support substrate, and a cover positioned on the spacer substrate. The cover cooperates with the support substrate to define a channel. The channel includes an inlet adjacent to the first end and opposite ends. Each electrode array is positioned in the channel adjacent to one of the ends.

13 Claims, 4 Drawing Sheets

U.S. PATENT DOCUMENTS

| | | | |
|---|---|---|---|
| 6,156,173 A * | 12/2000 | Gotoh et al. | 204/403.04 |
| 6,258,229 B1 | 7/2001 | Winarta et al. | 204/403 |
| 6,447,657 B1 * | 9/2002 | Bhullar et al. | 204/409 |
| 6,540,890 B1 * | 4/2003 | Bhullar et al. | 204/403.02 |
| 6,562,210 B1 * | 5/2003 | Bhullar et al. | 204/403.03 |
| 2003/0094367 A1 * | 5/2003 | Bhullar et al. | 204/403.1 |

FOREIGN PATENT DOCUMENTS

| | | |
|---|---|---|
| JP | 01-291153 | 11/1989 |
| JP | 04-264246 | 9/1992 |
| JP | 9-509740 | 9/1997 |
| JP | 10-170471 | 6/1998 |
| WO | WO 95/22597 | 8/1995 |
| WO | 00-60352 | 10/2000 |
| WO | 00/73778 | 12/2000 |
| WO | 00/73785 | 12/2000 |
| WO | WO 01 25775 A | 4/2001 |

OTHER PUBLICATIONS

Microline Solutions, LPKF Laser & Electronics AG; LPKF; Art.-Nr. 107658-1 (Jan. 2000) (4pp.).

* cited by examiner

BIOSENSOR

FIELD OF THE INVENTION

The present invention relates to a biosensor, more particularly to an electrochemical biosensor with a continuous capillary channel extending across electrodes.

BACKGROUND AND SUMMARY OF THE INVENTION

Electrochemical biosensors are known. They have been used to determine the concentration of various analytes from biological samples, particularly from blood. Electrochemical biosensors are described in U.S. Pat. Nos. 5,413,690; 5,762,770; 5,798,031; and 5,997,817 the disclosure of each of which is expressly incorporated herein by reference.

According to the present invention a biosensor is provided. The biosensor comprises a support substrate having first and second ends, electrodes positioned on the support substrate, the electrodes cooperating with one another to define electrode arrays situated adjacent to the first end, a spacer substrate positioned on the support substrate, and a cover positioned on the spacer substrate. The cover cooperates with the support substrate to define a channel a cover positioned on the spacer substrate, the cover cooperating with the support substrate to define a channel including a sample inlet adjacent to the first end and opposite ends. Each electrode array is positioned in the channel adjacent to one of the ends.

According to another aspect of the invention, a biosensor is provided. The biosensor comprises a support substrate, a first electrode set positioned on the support substrate, a second electrode set positioned on the support substrate, the first and second electrode sets being spaced-apart from one another, and a cover extending across the first and second electrode sets. The cover cooperates with the support substrate to define a generally linear capillary channel having opposing first and second ends and an inlet positioned between the ends and between the first and second electrode sets.

According to still another aspect of the invention, a method of forming a biosensor is provided. The method comprises the steps of forming spaced-apart electrode arrays on a surface of a support substrate, placing a spacer substrate on the support substrate across the electrode arrays, removing a portion of the spacer substrate to expose the electrode arrays, placing a cover on the spacer substrate to define a capillary channel having opposite ends and extending across the electrode arrays, and punching a notch through the support substrate, a portion of the spacer substrate, and the cover to form an inlet to the capillary channel so that the inlet is positioned between the opposite ends.

Additional features of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE INVENTION

The present invention relates to a biosensor and a method for manufacturing a biosensor that provides a manufacturer with precise and accurate dual channel position. The biosensor uses a continuous process to form a channel that extends across electrodes. Aspects of the invention are presented in FIGS. 1-5, which are not drawn to scale and wherein like components in the several views are numbered alike.

FIGS. 1-4 illustrate an aspect of the invention in the form of a biosensor 10 having an electrode-support substrate 12, an electrical conductor 13 positioned on the substrate 12 that is disrupted to define electrodes 14, 16, 18, a spacer substrate 20 positioned on substrate 12, and a cover 22 positioned on the spacer substrate 20. Biosensor 10 is preferably rectangular in shape. It is appreciated, however, that biosensor 10 can assume any number of shapes in accordance with this disclosure. Biosensor 10 is preferably produced from rolls of material, however, it is understood that biosensor 10 can be constructed from individual sheets in accordance with this disclosure. Thus, the selection of materials for the construction of biosensor 10 necessitates the use of materials that are sufficiently flexible for roll processing, but which are still rigid enough to give a useful stiffness to finished biosensor 10.

Figure 2:
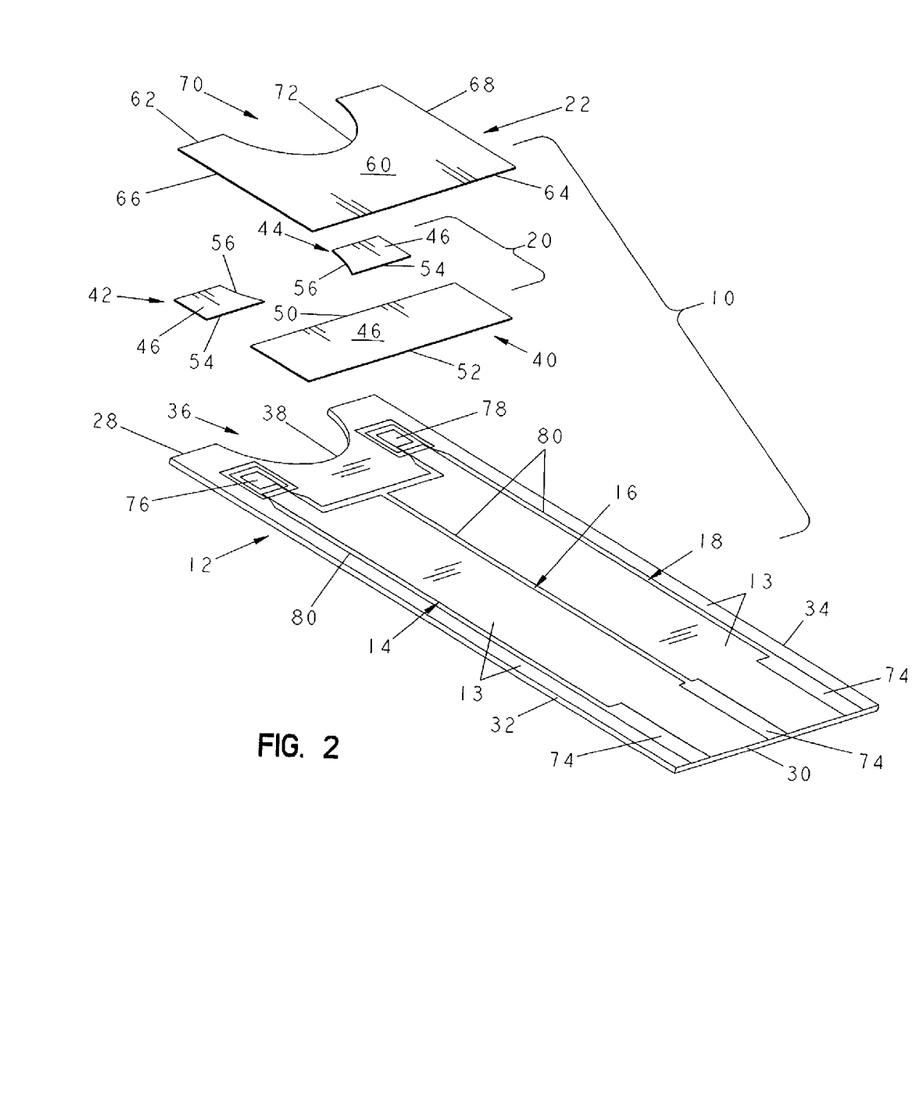
FIG. 2 is an exploded assembly view of the biosensor of FIG. 1, showing the biosensor including two spaced-apart electrode arrays positioned at one end, a spacer substrate including first, second, and third members and formed to extend about the electrode arrays.
Figure 3:
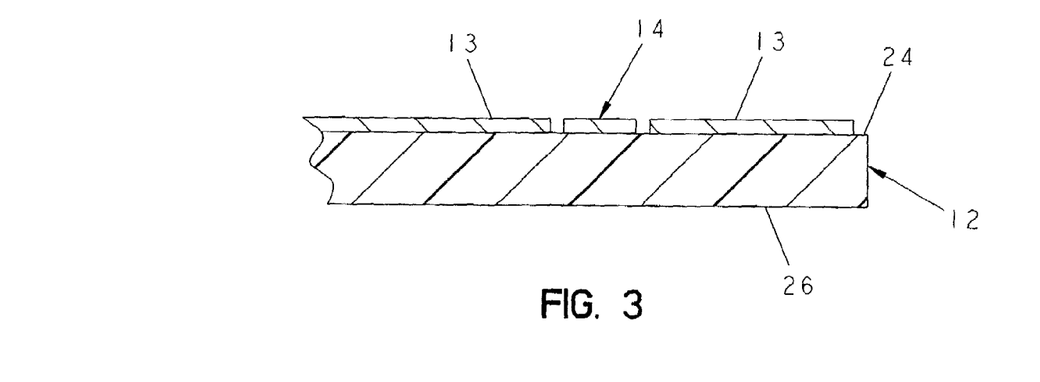
FIG. 3 is a view taken along lines 3-3 of FIG. 1A.

The electrode-support substrate 12 is shown in FIGS. 2 and 3. Referring to FIG. 3, substrate 12 includes a first surface 24 facing the spacer substrate 20 and a second surface 26. In addition, substrate 12 has opposite first and second ends 28, 30 and opposite edges 32, 34 extending between the first and second ends 28, 30. See FIG. 2. The first end 28 includes a notch 36 formed therein. A generally concave-shaped border 38 defines the notch 36. It is appreciated that the notch can take on a variety of shapes and sizes in accordance with this disclosure. Substrate 12 is generally rectangular in shape, it is appreciated, however, that support may be formed in a variety of shapes and sizes in accordance with this disclosure. Substrate 12 is formed of a flexible polymer and preferably from a flexible polymer and preferably from a polymer such as a polyester or polyimide, polyethylene naphthalate (PEN). A non-limiting example of a suitable PEN is 5 mil thick KALADEX®, a PEN film commercially available from E.I. DuPont de Nemours, Wilmington, Del., which is coated with gold by ROWO Coating, Henbolzhelm, Germany.

Electrodes 14, 16, 18 are created or isolated from conductor 13 on first surface 24 of substrate 12. Non-limiting examples of a suitable electrical conductor 13 include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, electrical conductor 13 is selected from the following materials: gold, platinum, palladium, iridium, or alloys of these metals, since such noble metals and their alloys are unreactive in biological systems. Most preferably, electrical conductor 13 is gold.

Electrodes 14, 16, 18 are isolated from the rest of the electrical conductor 13 by laser ablation. See FIG. 3. Techniques for forming electrodes on a surface using laser ablation are known. See, for example, U.S. patent application Ser. No. 09/411,940, filed Oct. 4, 1999, and entitled "LASER DEFINED FEATURES FOR PATTERNED LAMINATES AND ELECTRODE", the disclosure of which is expressly incorporated herein by reference. Preferably, electrodes 14, 16, 18 are created by removing the electrical conductor 13 from an area extending around the electrodes.

Therefore, electrodes 14, 16, 18 are isolated from the rest of the electrically-conductive material on substrate 12 by a gap having a width of about 25 µm to about 500 µm, preferably the gap has a width of about 100 µm to about 200 µm. Alternatively, it is appreciated that electrodes 14, 16, 18 may be created by laser ablation alone on substrate 12. It is appreciated that while laser ablation is the preferred method for forming electrodes 14, 16, 18 given its precision and sensitivity, other techniques such as lamination, screen-printing, or photolithography may be used in accordance with this disclosure.

As shown in FIG. 2, electrodes 14, 16, 18 cooperate with one another to define first and second electrode arrays 76, 78 and leads 80 that extend away from the first and second arrays 76, 78. Leads 80 extend from the arrays 76, 78 to contacts 74 at the second end 30 of the electrode-support substrate 12. It is appreciated that the leads extending from the arrays can be formed to have many lengths and extend to a variety of locations on the electrode-support substrate 12. It is appreciated that the configuration of the electrode arrays, the number of electrodes, as well as the spacing between the electrodes may vary in accordance with this disclosure and that a greater than two arrays may be formed as will be appreciated by one of skill in the art.

Spacer substrate 20 of biosensor 10 includes a first member 40 extending between the edges 32, 34 of the electrode-support substrate 12 and second and third members 42, 44 spaced-apart from the first member 40. Each member 40, 42, 44 includes an upper surface 46 and a lower surface 48 facing substrate 12. In addition, the first member 40 includes an inner edge 50 facing the second and third members 42, 44 and an outer edge 52. Second and third members 42, 44 include a first edge 54 facing the first member 40 and a second edge 56. The second edge 56 of the second and third members 42, 44 face one another.

Figures 1A, 1B:
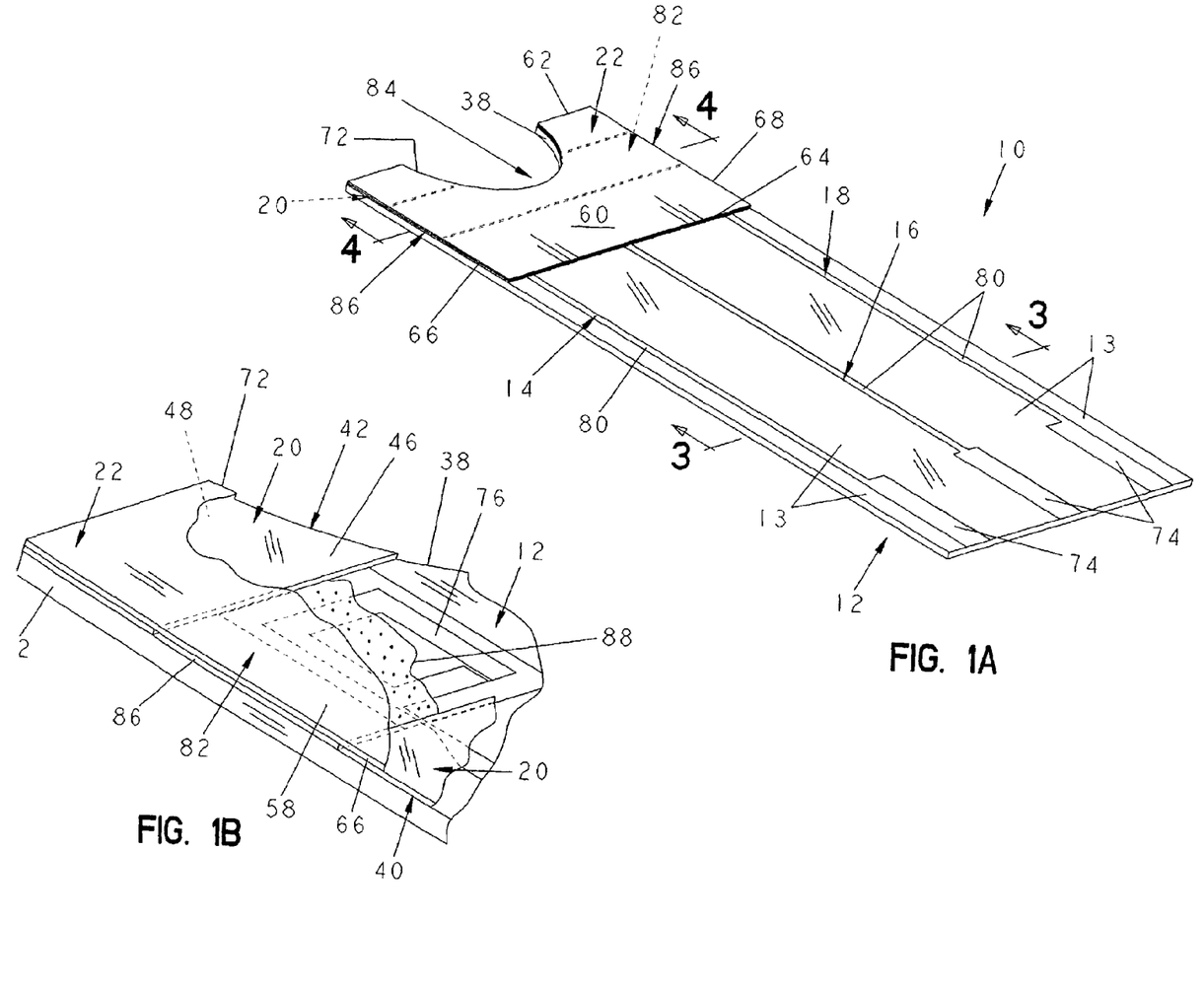
FIG. 1A is a perspective view of a biosensor in accordance with the present invention, showing the biosensor including a support substrate and a cover, each of which is formed to include a notch therein.
FIG. 1B is an enlarged perspective view of the biosensor of FIG. 1A with portions broken away.
Figure 4:
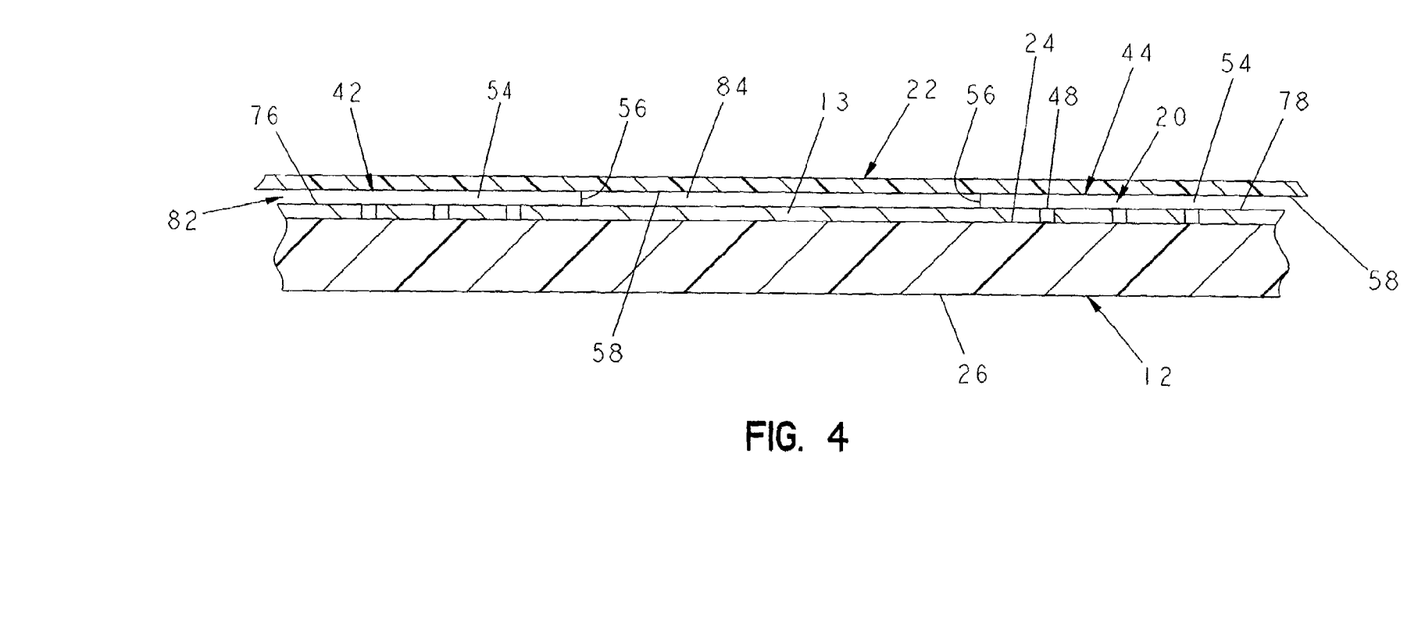
FIG. 4 is a view taken along lines 4-4 of FIG. 1A.

When spacer substrate 20 is coupled to substrate 12, as shown in FIGS. 1B and 4, the electrode arrays 76, 78 are positioned to lie between the first member 40 and the second and third members 42, 44. In addition, second and third members 42, 44 lie adjacent to border 38 of notch 36. Spacer substrate 20 is formed of a flexible polymer and preferably from a flexible polymer and preferably from a polymer such as an adhesive coated polyethylene terephthalate (PET)-polyester. A non-limiting example of a suitable PET is 3 mil (75 µm) thick white PET film both sides of which are coated with a pressure-sensitive adhesive (Product # ARcare 8877) commercially available from Adhesives Research, Inc. Glen Rock, Pa.

It is appreciated that spacer substrate 20 may be constructed of a variety of materials and may be coupled to the substrate 12 and the cover substrate 22 using a wide variety of commercially available adhesives. Additionally, when surface 24 of substrate 12 is exposed and not covered by electrical conductor 13, spacer substrate 20 may be coupled to substrate 12 by welding (heat or ultrasonic) in accordance with this disclosure. It is also appreciated that first surface 24 of substrate 12 may be printed with, for example, product labeling or instructions for use in accordance with this disclosure.

Cover substrate 22 is coupled to upper surface 46 of spacer substrate 20. See FIG. 1B. Cover substrate 22 includes an inner surface 58 facing spacer substrate 20 and an outer surface 60. In addition, cover 22 includes opposite first and second ends 62, 64 and edges 66, 68 extending between the first and second ends 62, 64. First end 62 includes a notch 70. A generally concave-shaped border 72 defines notch 70. It is appreciated that the notch can take on a variety of shapes and sizes in accordance with this disclosure. When biosensor 10 is assembled, cover 22 cooperates with the spacer support 20 and the electrode-support 12 to define a capillary channel 82.

Cover substrate 22 is generally rectangular in shape, it is appreciated, however, that the cover may be formed in a variety of shapes and sizes in accordance with this disclosure. Cover substrate 22 is formed from a flexible polymer and preferably from a polymer such as a polyester or polyimide. A non-limiting example of a suitable polymer is 3.9 mil (99 um) thick 3M hydrophilic Polyester film (3M Product #9971) commercially available from 3M Healthcare, St. Paul, Minn.

Referring now to FIGS. 1A and 1B, the capillary channel 82 is generally linear in shape and includes a sample inlet 84 and spaced-apart ends 86. As shown in FIG. 1A, ends 86 are positioned between edges 32, 66 and 34, 68 respectively. It is appreciated that while biosensor 10 illustratively includes ends 86 that serve as air outlets, it is appreciated that biosensor 10 can be formed to include any number of air outlets in accordance with this disclosure. The capillary channel 82 extends between borders 38, 72 and edges 32, 66 and 34, 68 respectively. Channel is also defined by inner edge 50 of first member 40 of the spacer substrate 20 and the first edges 54 of the second and third members 42, 44. See. FIG. 4. Therefore, when biosensor 10 is assembled, channel 82 extends across the electrode arrays 76, 78. See, for example FIG. 1B.

Electrochemical reagents 88 are positioned on first and second arrays 76, 78. Reagents 88 provide electrochemical probes for specific analytes. The choice of specific reagents 88 depend on the specific analyte or analytes to be measured, and are well known to those of ordinary skill in the art. An example of a reagent that may be used in biosensor 10 of the present invention is a reagent for measuring glucose from a whole blood sample. A non-limiting example of a reagent for measurement of glucose in a human blood sample contains 62.2 mg polyethylene oxide (mean molecular weight of 100-900 kilo Daltons), 3.3 mg NATROSOL 244M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in U.S. Pat. No. 5,997,817, the disclosure of which is expressly incorporated herein by reference.

Non-limiting examples of enzymes and mediators that may be used in measuring particular analytes in biosensor 10 are listed below in Table 1.

TABLE 1

| Analyte | Enzymes | Mediator (Oxidized Form) | Additional Mediator |
|---|---|---|---|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is contemplated that current, charge, impedance, conductance, potential, or other electrochemically indicated property of the sample might be accurately correlated to the concentration of the analyte in the sample with biosensor 10 in accordance with this disclosure.

A plurality of biosensors 10 are typically packaged in a vial, usually with a stopper formed to seal the vial. It is appreciated, however, that biosensors 10 may be packaged individually, or biosensors can be folded upon one another, rolled in a coil, stacked in a cassette magazine, or packed in blister packaging.

Biosensor 10 is used in conjunction with the following:
1. a power source in electrical connection with contacts 74 and capable of supplying an electrical potential difference between electrodes 14, 16 and 18, 16 sufficient to cause diffusion limited electro-oxidation of the reduced form of the mediator at the surface of the working electrode; and
2. a meter in electrical connection with contacts 74 and capable of measuring the diffusion limited current produced by oxidation of the reduced form of the mediator with the above-stated electrical potential difference is applied.

The meter will normally be adapted to apply an algorithm to the current measurement, whereby an analyte concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of each of which are expressly hereby incorporated by reference.

Many fluid samples may be analyzed. For example, human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues can also be assayed, along with foods, fermentation products and environmental substances, which potentially contain environmental contaminants. Preferably, whole blood is assayed with this invention.

Figure 5:
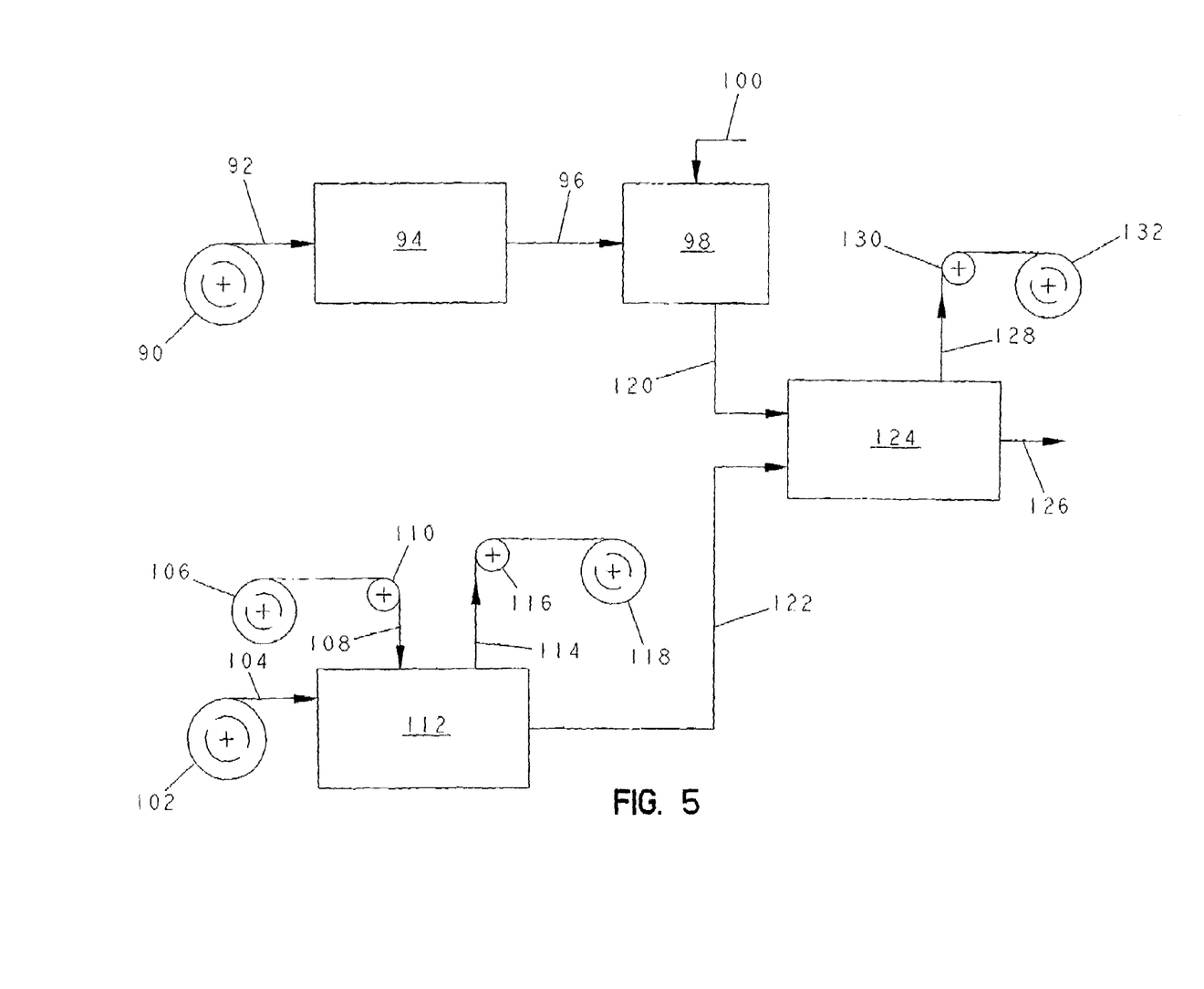
FIG. 5 is a diagrammatic view showing a manufacturing process for assembling the biosensor of FIG. 1.

To manufacture biosensor 10 a roll of metallized electrode support material 90 is fed as shown by arrow 92 in FIG. 5 through guide rolls into an ablation/washing and drying station 94. A laser system capable of ablating support 14 is known to those of ordinary skill in the art. Non-limiting examples of which include excimer lasers, with the pattern of ablation controlled by mirrors, lenses, and masks. A non-limiting example of such a custom fit system is the LPx-400, LPX-300 or LPX-200 commercially available from LPKF Laser Electronic GmbH, of Garbsen, Germany.

In the laser station 94, the metallic layer of the metallized film is ablated in a pre-determined pattern, to form a ribbon of isolated electrode sets on the electrode support material. To ablate electrodes 14, 16, 18 in 50 nm thick gold conductor 13, 90 mJ/cm² energy is applied. It is appreciated, however, that the amount of energy required may vary from material to material, metal to metal, or thickness to thickness. The ribbon is then passed through more guide rolls, with a tension loop and through an optional inspection system where both optical and electrical inspection can be made. The system is used for quality control in order to check for defects.

Upon leaving station 94, the metallized film is fed, as shown by arrow 96, into a reagent dispensing station 98. Reagents that have been compounded are fed, as shown by arrow 100, into dispensing station 98 where they are line-coated to cover part of the channel 82 using a custom-fit commercially available system from Iwashita Engineering Incorporated, Tokyo, Japan.

Alternatively, reagents that have been compounded are discretely applied in a liquid form to the center of respective first and second arrays 76, 78 using a custom-fit commercially available system from Fluilogic Systems, Espoo, Finland. When discrete application of reagents is selected, it is beneficial to create at least one recess (not shown) in the support substrate 12 surrounding the desired reagent-application site to retain the reagents 88 within the circumscribed reagent-application site boundary. Reagent application techniques are well known to one of ordinary skill in the art as described in U.S. Pat. No. 5,762,770, the disclosure of which is expressly incorporated herein by reference. It is appreciated that the reagents may be applied to arrays 76, 78 in a liquid or other form and dried or semi-dried onto arrays 76, 78 in accordance with this disclosure.

In a separate process, a double-sided pressure-sensitive film with dual release liners 102 is fed, as shown by arrow 104, into a lamination & kiss-cutting station 112. At the same time, a roll of cover substrate material 106 is fed over a guide roll 110 as shown by arrow 108 into the station 112. In the station 112, the release liner is removed from the upper surface 46 as shown by arrow 114, from the station 112 and rewound over guide roll 116 into a roll 118 for discard. In the station 112, the upper surface 46 of the film 102 is applied to the inner surface 58 of cover substrate material 106. Next, the film is kiss cut and a portion of the film is removed leaving behind first member 40 and a second/third member strip (not shown) coupled to the cover material. The cover material is exposed between the first member 40 and the second/third member.

The cover material/spacer substrate subassembly is fed, as shown by arrow 122, into a sensor lamination & cut/pack station 124. The reagent-coated electrode-support substrate material is fed from station 98, as shown by arrow 120, into the sensor lamination & cut/pack station 124 as well. The remaining release liner is removed from the spacer substrate and the spacer substrate is positioned on the electrode-support substrate material so that the electrode arrays 76, 78 lie between the first member 40 and the second/third member strip. Once assembled, notches 36, 70 are punched through electrode-support substrate material, the second/third member of the spacer substrate, and the cover substrate material. This cut forms the sample inlet 84 to the capillary channel 82.

Next, the resulting assembled material is cut to form individual biosensors 10, which are sorted and packed into vials, each closed with a stopper, to give packaged biosensor strips.

In use, a user of biosensor 10 places a finger having a blood collection incision against borders 38, 72 of notches 36, 70. Capillary forces pull a liquid blood sample flowing from the incision into the sample inlet 84 and through the capillary channel 82 across the reagents 88 and the arrays 76, 78. The liquid blood sample dissolves the reagents and engages the arrays 76, 78 where the electrochemical reaction takes place.

In use, after the reaction is complete, a power source (e.g., a battery) applies a potential difference between the electrodes 14, 16 and 18, 16 respectively. When the potential difference is applied, the amount of oxidized form of the mediator at the reference electrode and the potential difference must be sufficient to cause diffusion-limited electro-oxidation of the reduced form of the mediator at the surface of the working electrode. A current measuring meter (not shown) measures the diffusion-limited current generated by the oxidation of the reduced form of the mediator at the surface of the working electrode.

The measured current may be accurately correlated to the concentration of the analyte in sample when the following requirements are satisfied:
1. The rate of oxidation of the reduced form of the mediator is governed by the rate of diffusion of the reduced form of the mediator to the surface of the working electrode.
2. The current produced is limited by the oxidation of reduced form of the mediator at the surface of the working electrode.

The processes and products described above include disposable biosensor 10 especially for use in diagnostic devices. Also included, however, are electrochemical sensors for non-diagnostic uses, such as measuring an analyte in any biological, environmental, or other sample. As discussed above, biosensor 10 can be manufactured in a variety of shapes and sizes and be used to perform a variety of assays, non-limiting examples of which include current, charge, impedance conductance, potential or other electrochemical indicative property of the sample applied to biosensor.

Although the invention has been described in detail with reference to a preferred embodiment, variations and modifications exist within the scope and spirit of the invention, on as described and defined in the following claims

What is claimed is:
1. A biosensor comprising
a support having first and second ends,
electrodes positioned on the support, the electrodes cooperating with one another to define electrode arrays situated adjacent to the first end,
a spacer having individual members, and
a cover cooperating with the support to define a capillary channel extending between the individual members, the channel having opposing ends outlets and a concave inlet extending from the first end of the support and being positioned between the opposing outlets of the channel, each electrode array being positioned in the channel adjacent to one of the opposing outlets.

2. The biosensor of claim 1 wherein the individual members of the spacer include spaced-apart first, second and third members and the channel extends between the first, second, and third members.

3. A biosensor comprising:
a support having a first edge,
first and second electrode sets positioned on the support spaced-apart from one another,
a spacer having individual members, and
a cover having a second edge, the cover extending across the first and second electrode sets, the cover cooperating with the support to define a generally linear capillary channel extending between the individual members, the channel having opposing first and second outlets and an inlet aligned with the first edge of the support and the second edge of the cover, between the outlets of the channel, and between the first and second electrode sets.

4. The biosensor of claim 3 wherein the individual members include a first member extending between the outlets of the channel.

5. The biosensor of claim 4 wherein the members include a second member positioned between one outlet and the inlet and a third member positioned between the opposite outlet and the inlet.

6. The biosensor of claim 4 wherein the members include second and third members spaced-apart from the first member and the channel extends between the first, second, and third members.

7. The biosensor of claim 3 wherein the cover and the support are formed to include a notch in general alignment with one another.

8. The biosensor of claim 7 wherein each notch is generally concave in shape.

9. The biosensor of claim 7 wherein the inlet intersects the notches.

10. A biosensor comprising
a support having first and second ends,
electrodes positioned on the support, the electrodes cooperating with one another to define electrode arrays situated adjacent to the first end,
a spacer having individual first, second, and third members, and
a cover cooperating with support to define a capillary channel, the channel extending between the three members and having an inlet positioned between the second and third members adjacent to the first end of the support and spaced-apart first and second opposite outlets, the first opposite outlet being positioned between the first and second members and the second opposite outlet being positioned between the first and third members, each electrode array being positioned in the channel adjacent to one of the opposite outlets.

11. The biosensor of claim 10 wherein the cover and the support are formed to include a notch in general alignment with one another.

12. The biosensor of claim 11 wherein each notch is generally concave in shape.

13. The biosensor of claim 11 wherein the inlet intersects the notches.

* * * * *